United States Patent
Weinberg

(10) Patent No.: US 11,077,313 B2
(45) Date of Patent: Aug. 3, 2021

(54) ELECTRICITY ENERGY HARVESTING WITH LIQUID CRYSTAL-MAGNETIC PARTICLE COMPOSITE PARTICLES

(71) Applicant: Weinberg Medical Physics, Inc., North Bethesda, MD (US)

(72) Inventor: Irving N. Weinberg, North Bethesda, MD (US)

(73) Assignee: WEINBERG MEDICAL PHYSICS INC

( * ) Notice: Subject to any disclaimer, the term of this patent is extended or adjusted under 35 U.S.C. 154(b) by 446 days.

(21) Appl. No.: 16/028,984

(22) Filed: Jul. 6, 2018

(65) Prior Publication Data

US 2019/0009100 A1  Jan. 10, 2019

Related U.S. Application Data

(60) Provisional application No. 62/529,864, filed on Jul. 7, 2017.

(51) Int. Cl.
*A61N 1/40* (2006.01)
*H02N 1/08* (2006.01)

(52) U.S. Cl.
CPC .............. *A61N 1/40* (2013.01); *H02N 1/08* (2013.01)

(58) Field of Classification Search
CPC .... A61N 1/40; A61N 1/37205; A61N 1/3787; A61N 2/006; A61N 5/0625; H02N 1/08; A61B 5/0515; A61B 5/6846; H02K 35/02; Y10T 29/49009
See application file for complete search history.

(56) References Cited

U.S. PATENT DOCUMENTS

| | | | | |
|---|---|---|---|---|
| 6,768,246 | B2 * | 7/2004 | Pelrine | F02G 1/043 310/317 |
| 8,221,439 | B2 * | 7/2012 | Dlugos, Jr. | A61F 5/0059 606/151 |
| 9,095,716 | B2 * | 8/2015 | Makdissi | A61N 1/36542 |
| 2005/0256549 | A1 * | 11/2005 | Holzer | H02K 35/02 607/35 |
| 2009/0212645 | A1 * | 8/2009 | Theuss | H02K 35/02 310/15 |
| 2009/0281600 | A1 * | 11/2009 | Lemieux | H02K 33/18 607/61 |
| 2010/0217354 | A1 * | 8/2010 | Weiss | A61N 1/3785 607/61 |
| 2012/0078322 | A1 * | 3/2012 | Dal Molin | A61N 1/37288 607/32 |
| 2012/0283807 | A1 * | 11/2012 | Deterre | A61N 1/3975 607/116 |
| 2016/0129276 | A1 * | 5/2016 | Fried | A61N 2/006 600/12 |

* cited by examiner

*Primary Examiner* — Kaylee R Wilson
(74) *Attorney, Agent, or Firm* — Barnes & Thornburg LLP

(57) ABSTRACT

A method and apparatus generate electrical currents and/or voltage in tissue using devices composed of liquid crystals and magnetic particles. An instrument applies one or more magnetic fields to the devices to produce electrical energy.

16 Claims, 2 Drawing Sheets

ELECTRICITY ENERGY HARVESTING WITH LIQUID CRYSTAL-MAGNETIC PARTICLE COMPOSITE PARTICLES

CROSS REFERENCE AND PRIORITY CLAIM

This patent application claims priority to U.S. Provisional Application Provisional Patent Application No. Patent Application Ser. No. 62/529,864, "Electricity Energy Harvesting with Liquid Crystal-magnetic Particle Composite Particles," filed Jul. 7, 2017, the disclosure of which being incorporated herein by reference in its entirety.

FIELD OF USE

Disclosed embodiments provide a method and apparatus for stimulating living tissue.

BACKGROUND

Conventionally, work has been done on energy harvesting with liquid crystals, in which mechanical motion on the liquid crystals is converted into electrical energy, as taught by the 2016 publication entitled "Liquid-crystal-enhanced electrostatic vibration generator" by Kittipaisalsilpa, K., Kato, T. & Suzuki, Y., 2016. LIQUID-CRYSTAL-ENHANCED ELECTROSTATIC VIBRATION Dept. of Mechanical Engineering, The University of Tokyo, Tokyo, JAPAN, (January), pp. 37-40. (Kittipaisalsilpa et al.; incorporated herein by reference in its entirety). The apparatus described in that publication was a planar configuration of liquid crystal material sandwiched between electrodes.

A similar configuration was analyzed theoretically in the 2011 AIP Advances publication entitled "The limits of flexoelectricity in liquid crystals" by F. Castles. See AIP Advances, 1(3), pp. 1-7. (incorporated herein by reference in its entirety). Magnetic particles immersed in liquid crystals have been shown capable of manipulating the crystal orientation. See Wang, M. et al., 2014. Magnetically Actuated Liquid Crystals. Nano Letters, 14, pp. 3966-3971 (incorporated herein by reference in its entirety).

SUMMARY

Disclosed embodiments provide a method and apparatus for generating electrical current and/or voltage in tissue using particles which include liquid crystals and magnetic particles.

In accordance with at least one embodiment, methodologies and apparatuses may use of magnetic particles within liquid crystals in one or more particles to transmit mechanical energy so that electrical energy is produced from the particle(s).

BRIEF DESCRIPTION OF FIGURES

The detailed description particularly refers to the accompanying figures in which.

DETAILED DESCRIPTION

Innovative concepts disclosed in the present application build on innovations described in U.S. Non-Provisional patent application Ser. No. 15/964,289, entitled "APPARATUS AND METHOD FOR REMOTE DETECTION OF ELECTRIC FIELDS IN LIVING TISSUES USING MAGNETIC PARTICLES AND LIQUID CRYSTALS," filed Apr. 27, 2018, the disclosure of which being incorporated herein by reference in its entirety. The innovative concepts disclosed in that earlier application relate to the use of liquid crystals/magnetic particles to detect the electrical state of tissues; to the contrary, presently disclosed embodiments pertain to how a similar particle configuration can be used to change the electrical state of the tissue of a subject.

For the purposes of this specification, the term "subject" includes but is not limited to a human or other animal with or without illness. Likewise, the term "liquid crystal component" includes but is not limited to any material with electrical properties that are dependent on orientation, for example, a liquid crystal in the form of an electret. An electret is a polarized piece of dielectric material, analogous to a permanent magnet, for example, as described by Kittipaisalsilpa et al.

Conventionally, magnetic particles have been placed in liquid crystals, as taught by G. Cordoyiannis et al in the journal Liquid Crystals 43:3, pp. 314-319, entitled "The effect of magnetic nanoparticles upon the smectic-A to smectic-C* phase transition." See Cordoyiannis, G. et al., 2016; incorporated herein by reference in its entirety).

In accordance with presently disclosed embodiments, an apparatus may include at least one device containing at least one liquid crystal and at least one magnetic particle, wherein the device is positioned in a living tissue which may be stimulated or modulated electrically.

Additionally, in accordance with the presently disclosed embodiments, the apparatus may also include an instrument placed outside the subject's living tissue.

In accordance with the disclosed embodiments, the referred to at least one magnetic particle is a structure smaller than 100 micrometers in any dimension, and containing one or more materials that may be magnetized by an applied magnetic or electromagnetic field.

In accordance with at least some embodiments, the at least one magnetic particle may be smaller than 100 microns in its largest dimension, and may be smaller than 1 micron in its largest dimension, and may be smaller than 10 nm in its largest dimension, and may be smaller than 1 nm in its largest dimension.

Figure 1:
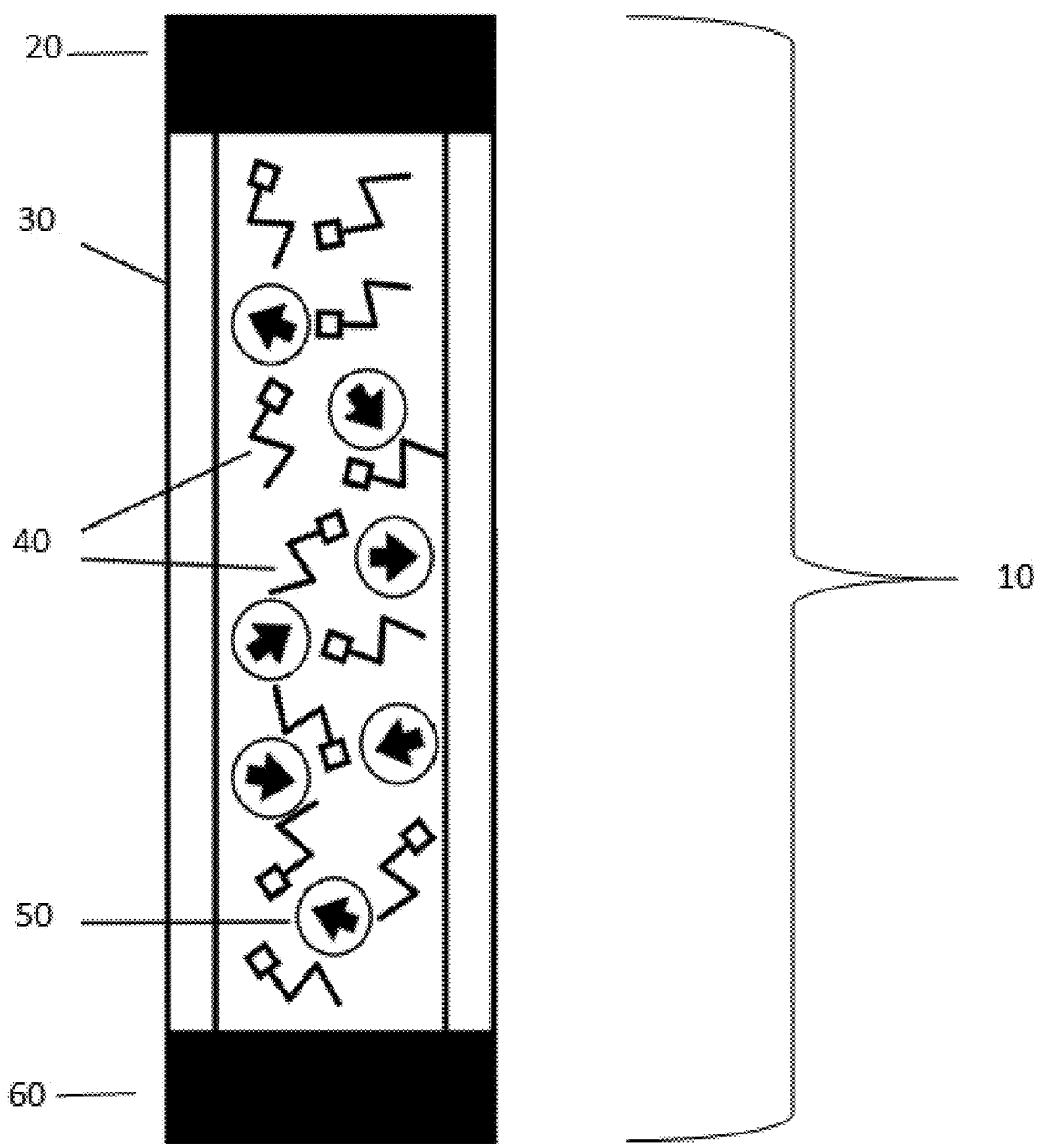
FIG. 1 shows an example of the device component of the apparatus.

FIG. 1 shows an example of the device component of the apparatus. In this example, the device 10 is implemented using a cylindrical capsule with sidewalls 30, said capsule containing both liquid crystal materials 40 and magnetic particles 50. The capsule is shown with optional electrically conductive caps 20 and 60. In accordance with the disclosed embodiments, the device 10 is smaller than 100 microns in its largest dimension, may be smaller than 1 micron, may be smaller than 10 nm, and/or may be smaller than 1 nm. It is understood that the device 10 may be introduced into a subject's body, said introduction being intra-nasal, intravenous, oral, or by some other route.

For the purposes of this specification, the term liquid crystal solution includes both the case in which the liquid crystals are present in the device 10 without another liquid material, as well as the case where the liquid crystals are in another liquid material (for example water).

FIG. 1 shows the device without a magnetic field applied to it.

Figure 2:
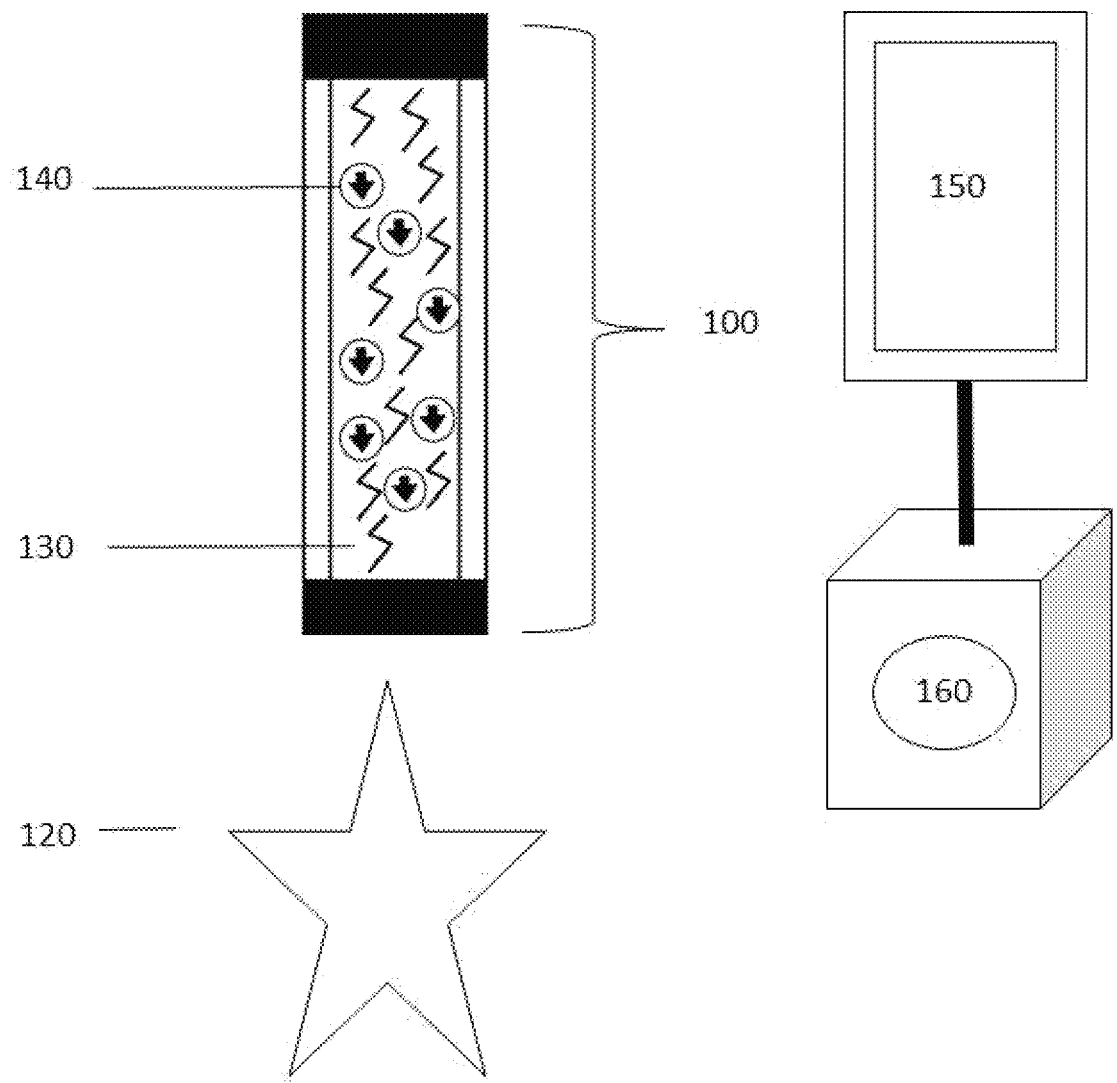
FIG. 2 shows an example of the response of the device illustrated in FIG. 1 to an applied magnetic field.

FIG. 2 shows an example of the response of the device 100 (which is the same device illustrated in FIG. 1 as 10 but with an applied magnetic field). As shown in FIG. 2, magnetic particles 140 (illustrated in FIG. 1 as 40) are oriented by the applied magnetic field to orient the liquid crystals 130 in a direction that may be parallel to the applied magnetic field. Alternatively, the direction may have been set by a prior magnetic or electromagnetic field, or may be a result of a physiological process (for example diffusion). Said direction is termed "preferential" for the purposes of this specification, since the user of the invention will have had a preference as to which direction it should be, and will have applied magnetic or electromagnetic fields to the tissue in order to create the preferential direction. The preferential direction may be different for different devices 100 in the tissue. The applied magnetic field may have been created or otherwise modified by magnets (permanent, electropermanent, superconducting, or other types of magnets) placed external to the subject's body.

Operations performed to implement a preferential orientation cause an electric field to be applied to components of living tissue 120. The changes in magnetic particle ordering may be implemented and detected with at least one sensor 150, which, in at least one embodiment, may be positioned outside the living tissue. Examples of sensor 150 include components of a magnetic resonance imaging (MRI) device, or of a magnetic particle imaging (MPI) device. In combination with the innovations previously disclosed in U.S. Non-Provisional patent application Ser. No. 15/964,289, the electrical orientation of one or more constituents of particles 100 can be detected remotely with a sensor 150 to describe the electrical activity of the particles 100 or of components of living tissue 120. For example, the magnetization of the magnetic particles 140 may be used to report to an external MRI the direction of the magnetic particles 140 and thereby describe the orientation of liquid crystals 130 or of the entire particle 100.

In accordance with at least one embodiment, the at least one sensor 150 may be connected electrically to a computer processor 160, which may be used to display information about the anatomy, electrical, and magnetic activity of the particles 100 and of components of living tissue 120.

In accordance with at least one disclosed embodiment one or more sections of the device 10/100 may be coated with a biocompatible material, for example, polyethylene glycol.

One or more sections of the device 10/100 may be coated with a material that enhances transport across physiological barriers, for example ICAM (see Hsu, J. et al., 2012. Enhanced delivery of α-glucosidase for Pompe disease by ICAM-1-targeted nanocarriers: comparative performance of a strategy for three distinct lysosomal storage disorders. Nanomedicine: nanotechnology, biology, and medicine, 8(5), pp. 731-9) (incorporated herein by reference in its entirety) for transport across the blood-brain barrier. The blood-brain barrier is a physiological barrier that prevents materials from entering the brain from the circulatory system. For the purposes of this specification, the term "into the brain" is meant to include transport of particles into the brain that bypass or cross the blood-brain barrier from the circulation or from the nose or via other routes. One or more sections of the device 10/100 may be coated with a material to enhance biocompatibility, for example, L1 protein. See Kuo, L. E. et al., 2007. Neuropeptide Y acts directly in the periphery on fat tissue and mediates stress-induced obesity and metabolic syndrome. Nature medicine, 13(7), pp. 803-811 (incorporated herein by reference in its entirety).

One or more sections of the device 10/100 may contain features that enhance propulsion or rotation, as taught by Mair, L. O. et al., 2015. Analysis of Driven Nanorod Transport Through a Biopolymer Matrix. Journal of magnetism and magnetic materials, 380, pp. 295-298 (incorporated herein by reference in its entirety) and Nacev, A., Stepanov, P. Y. & Weinberg, I. N., 2015. Dynamic Magnetic Inversion Concentrates Ferromagnetic Rods to Central Targets. Nano letters (incorporated herein by reference in its entirety).

In accordance with at least one embodiment, living tissue 120 may be an assembly of neurons in an animal or human brain. The electrical activity may be from non-neural sources, for example a muscle cell. In accordance with at least one embodiment, the one or more devices 10/100 may be placed less than 100 microns from one or more neurons of the living tissue 120.

In accordance with at least one embodiment, one or more devices may be coated with a material (for example, a lipophilic coating) that may promote insertion of at least one portion of the device across the neural membrane. Thus, it should be understood that the liquid crystal device may be more readily incorporated into components in the living tissue (for example in the neural membrane) through judicious coating of the device (for example with a lipophilic coating as described above).

For the purposes of this disclosure, the terms "electrical field," or "electric field" refer to electrical energy that may be in the form of voltage or current or field. More specifically, since all neurons are electrically excitable, due to maintenance of voltage gradients across their membranes (for example, using metabolically driven ion pumps), disclosed embodiments may be used to change the cross-membrane voltage to alter the function of voltage-dependent ion channels or other physiological mechanisms that either excite or suppress neuronal activation.

Thus, a magnetic field may be applied to particle 100 by a device external to the body in order to change the orientation of one or more magnetic particles 140, which in turn may impose a change of orientation of liquid crystal/electret material 130. Accordingly, this orientation may cause an electrical field to be applied to tissue 100 in the body of a subject. As a result, this electrical field can cause a change in the electrical state of tissue 120.

For the purposes of this disclosure, the mechanism of conversion of mechanical energy from the magnetic particles into electrical energy may be understood as being due to a change in configuration of the liquid crystals. However, it should be understood that other mechanisms (for example, quantum mechanical) may be responsible for that conversion within the described configuration, and that the specific details as to exactly how the conversion occurs are not critical to the technical utility of the innovative concepts disclosed herein.

It should be understood that liquid crystals are present in many living creatures, as taught by D. Chapman in the book "Liquid crystals and cell membranes," Ann. N.Y. Acad. Sci., vol. 137, no. 2 Biological Me, pp. 745-754, July 1966 (incorporated herein by reference in its entirety). Neuronal membranes may be considered to be liquid crystals, and, in that role, changes within the liquid crystals lead to altered electrical potentials that can cause neuronal stimulation. Thus, it should be understood that the alteration of liquid crystal configuration with magnetic particles under the control of a magnetic field applied by an instrument externally to the nervous system of interest may, therefore, alter the electrical properties of the liquid crystal that is near or in the nervous system, so as to stimulate or otherwise modulate the electrical activity of the nervous system or other components of living tissue. Further, it should be understood that such alteration of electrical activity in living tissue may be monitored or otherwise controlled by sensing the voltage in the living tissue using the at least one sensor and computer processor configuration disclosed herein.

An example of the use of magnetic nanoparticles to affect the electric fields from liquid crystals is given by S. Ghosh et al in the scientific paper published in European Letters Association (EPL) on Nov. 10, 2011, volume 96(4), p. 47003, entitled "Effect of multiferroic BiFeO3 nanoparticles on electro-optical and dielectric properties of a partially fluorinated orthoconic antiferroelectric liquid crystal mixture" (incorporated herein by reference in its entirety).

Other examples of coupling between the magnetic properties of magnetic particles and the electric properties of liquid crystals are taught in Rožič, B. et al., 2011. Multiferroic Behaviour in Mixtures of the Ferroelectric Liquid Crystal and Magnetic Nanoparticles. Molecular Crystals and Liquid Crystals, 545(1), p. 99/[1323]-104/[1328] (incorporated herein by reference in its entirety); and the paper by P. Ganguly et al in Applied Physics Letters 108(18), p. 182905, entitled "Nanoparticles induced multiferroicity in liquid crystal" (incorporated herein by reference in its entirety).

It should be understood that the classes of magnetic and liquid crystal materials that may be used to implement the currently disclosed innovative concepts include multiferroic, ferroelectric and antiferroelectric.

Note that the figures illustrate the orientations of the magnetic particles and liquid crystals as being in a single direction. However, it should be understood that the orientations may be in multiple directions, so long as those directions cumulatively result in generation of an electrical field.

Further, it should be understood that either or both of the at least one sensor 150 and the computer processor 160 may be either within or external to the body containing living tissue 120.

As explained briefly above, in accordance with at least one embodiment, the device 10/100 may take the form of a cylindrical capsule filled with liquid crystal and magnetic particles contained within the capsule. In such an implementation, the ends of the cylindrical capsule may contain a conductive material to couple effectively with tissues in the vicinity of the device 10/100. For the purposes of this specification, the term "vicinity of the device" refers to being within a distance of less than 1 mm. This distance may be much smaller, for example, one micron or one nanometer. Examples of such conductive materials include gold, platinum, polypyrrole, or a composite of such materials. One or more sections of the device may be composed of an insulating material such as silicon dioxide.

FIG. 1 shows electrically conducting caps 20 and 60. It is understood that one or both of these caps may not be required to impart an electrical field on tissue 120.

It should be understood that in accordance with at least one exemplary operation of the disclosed innovations, a plurality of the devices 10/100 may be administered to, introduced to, or positioned within the living tissue. For example, to modify the electrical activity in the peripheral nerves of a human or other animal, billions of devices may be injected intravenously. The devices might be administered intranasally in order to access the brain, as taught by Weinberg, I. et al., 2012. Non-Invasive Image-Guided Brain Access with Gradient Propulsion of Magnetic Nanoparticles. In IEEE Medical Imaging Meeting. Anaheim, Calif. (incorporated herein by reference in its entirety), or through other means (for example, by intravenous, intrathecal, intracranial, or other forms of injection into a body).

Technical utility is provided by the apparatus, incorporated device, and methodologies in that they may be used to modulate electrical activity in a living tissue without the need for a solid connection (e.g., wire, lead or conventionally known electrode). For the purposes of this specification, this property is referred to as "untethered."

It should be understood that device 10/100 may be used in conjunction with, as described above, other components, for example a computer processor. In addition, the disclosed apparatus may include, utilize or be used in conjunction with a power supply and/or coils for generating magnetic and/or electromagnetic fields, in order to generate an electrical field. Thus, although not shown in detail herein, it should be understood that the disclosed embodiments may be used in conjunction with a support structure that may hold coils for exciting the device 10/100 within the living tissue, wherein the support structure includes coils used to apply the electric field as well as, optionally, an imaging system to enable positioning and/or monitoring of the device 10/100 in the living tissue and/or the living tissue itself. Moreover, it should be understood that an associated display system is not shown but should be understood to be present in order to view images produced by the imaging system.

It should be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and nonvolatile storage technologies without departing from certain embodiments. Such alternative storage devices should be considered equivalents.

While certain illustrative embodiments have been described, it is evident that many alternatives, modifications, permutations and variations will become apparent to those skilled in the art in light of the foregoing description. Accordingly, the various embodiments of, as set forth above, are intended to be illustrative, not limiting. Various changes may be made without departing from the spirit and scope of the invention.

What is claimed:

1. A system comprising:
    at least one device being no more than 100 microns in any single dimension, containing at least one magnetic particle in a liquid crystal solution, and configured to be positioned in living tissue; and
    an instrument, configured to be positioned internal or external to a body containing the living tissue, for applying a magnetic field to the at least one device to produce an electrical field for application to the living tissue.

2. The system of claim 1, wherein the at least one device is untethered within the living tissue.

3. The system of claim 1, wherein one or more sections of the at least one device are coated with a biocompatible material.

4. The system of claim 1, wherein one or more sections of the at least one device are coated with a material to enhance transport to or through the living tissue.

5. The system of claim 1, wherein one or more sections of the at least one device are coated with a material to enhance transport into the brain.

6. A method for changing an electrical state of at least one device present in living tissue, the method comprising:
    positioning the at least one device within the living tissue, wherein the at least one device is no more than 100 microns in any single dimension and contains at least one magnetic particle in a liquid crystal solution; and
    applying one or more magnetic fields to the at least one device to produce electrical energy.

7. The method of claim 6, wherein the at least one device is untethered within the living tissue.

8. The method of claim 6, wherein one or more sections of the at least one device are coated with a biocompatible material.

9. The method of claim 6, wherein one or more sections of the at least one device are coated with a material to enhance transport to or through the living tissue.

10. The method of claim 6, wherein one or more sections of the at least one device are coated with a material to enhance transport into the brain.

11. A method for altering and monitoring an electrical state of at least one device present in living tissue, the method comprising:
    positioning the at least one device within the living tissue, wherein the at least one device is no more than 100 microns in any single dimension and contains at least one magnetic particle in a liquid crystal solution;
    applying one or more magnetic fields to the at least one device to produce electrical energy; and
    remotely sensing a status of the at least one device.

12. The method of claim 11, wherein the status is a magnetic status of the at least one device.

13. The method of claim 11, wherein the at least one device is untethered within the living tissue.

14. The method of claim 11, wherein one or more sections of the at least one device are coated with a biocompatible material.

15. The method of claim 11, wherein one or more sections of the at least one device are coated with a material to enhance transport to or through the living tissue.

16. The method of claim 11, wherein one or more sections of the at least one device are coated with a material to enhance transport into the brain.

* * * * *